United States Patent [19]

Mehta

[11] Patent Number: 5,258,042
[45] Date of Patent: Nov. 2, 1993

[54] INTRAVASCULAR HYDROGEL IMPLANT

[75] Inventor: Bharat Mehta, West Bloomfield, Mich.

[73] Assignee: Henry Ford Health System, Detroit, Mich.

[21] Appl. No.: 809,265

[22] Filed: Dec. 16, 1991

[51] Int. Cl.$^5$ .................... A61F 2/54; A61F 2/04; A61F 2/06; A61M 31/00
[52] U.S. Cl. .................... 623/66; 623/1; 623/12; 604/49; 606/108
[58] Field of Search .................... 623/1, 2, 12, 66, 500, 623/901; 604/96, 51-54; 606/108, 153

[56] References Cited

U.S. PATENT DOCUMENTS

| | | | |
|---|---|---|---|
| 4,140,126 | 2/1979 | Choudhury | 623/1 X |
| 4,286,341 | 9/1981 | Greer et al. | 623/1 |
| 4,562,596 | 1/1986 | Kornberg | 623/1 |
| 4,577,631 | 3/1986 | Kreamer | 623/1 X |
| 4,663,358 | 5/1987 | Hyon et al. | 521/64 |
| 4,734,097 | 3/1988 | Tanabe et al. | 623/1 |
| 4,740,207 | 4/1988 | Kreamer | 623/1 |
| 4,852,568 | 8/1989 | Kensey | 623/1 X |
| 4,990,582 | 2/1991 | Salamone | 526/245 |
| 5,078,726 | 1/1992 | Kreamer | 623/1 X |
| 5,084,065 | 1/1992 | Weldon et al. | 623/1 |

FOREIGN PATENT DOCUMENTS

| | | | |
|---|---|---|---|
| 0107055 | 5/1984 | European Pat. Off. | 623/11 |
| 0441516 | 8/1991 | European Pat. Off. | 623/11 |
| 2139898 | 11/1984 | United Kingdom | 623/11 |

OTHER PUBLICATIONS

Serbinenko F. A. "Balloon Catheterization and . . . Cerebral Vessels", J. Neurosurg. 1974; 41: 125-145.
Romodanov A. P., et al., "Intravascular Occlusion . . . Catheter", In Advances & Technical Standards, vol. 9, 1982; 25-49.
Hieshima G. B. et al., "A Detachable . . . Occlusion", Radiology 1981; 138: 227-228.
Guglielmi G., et al., "Electrothrombosis of . . . Results", J. Neurosurg. 1991; 75: 1-7.
Guglielmi G., et al., "Electrothrombosis of . . . Experience", J. Neurosurg. 1991; 75: 8-14.
Sigwart V., et al., "Intravascular . . . Angioplasty", N. England J. Med., 1987; 316: 701-706.
Duprat G. Jr., et al., "Self Expanding . . . Evaluation", Radiology 1987; 162: 469-472.
Strecker E. P., "Flexible, Balloon . . . Results", Radiology 1988; 169: 388.
Paper No. 199, American Society of Neuroradiology, 29th Annual Meeting, Washington, D.C., Jun. 9-14, 1991.
Paper No. 200, American Society of Neuroradiology, 29th Annual Meeting, Washington, D.C., Jun. 9-14, 1991.

*Primary Examiner*—Randall L. Green
*Assistant Examiner*—Dinh X. Nguyen
*Attorney, Agent, or Firm*—Barnes, Kisselle, Raisch, Choate, Whittemore & Hulbert

[57] ABSTRACT

A vascular structure, including an artery, vein or vessel, with a peripheral wall defining a cavity and having a localized abnormal wall is treated by inserting a device of a hydrogel material into the cavity; and then hydrating and expanding the hydrogel material until the device occludes the localized abnormal wall, sealing it from the cavity of the vascular structure.

6 Claims, 3 Drawing Sheets

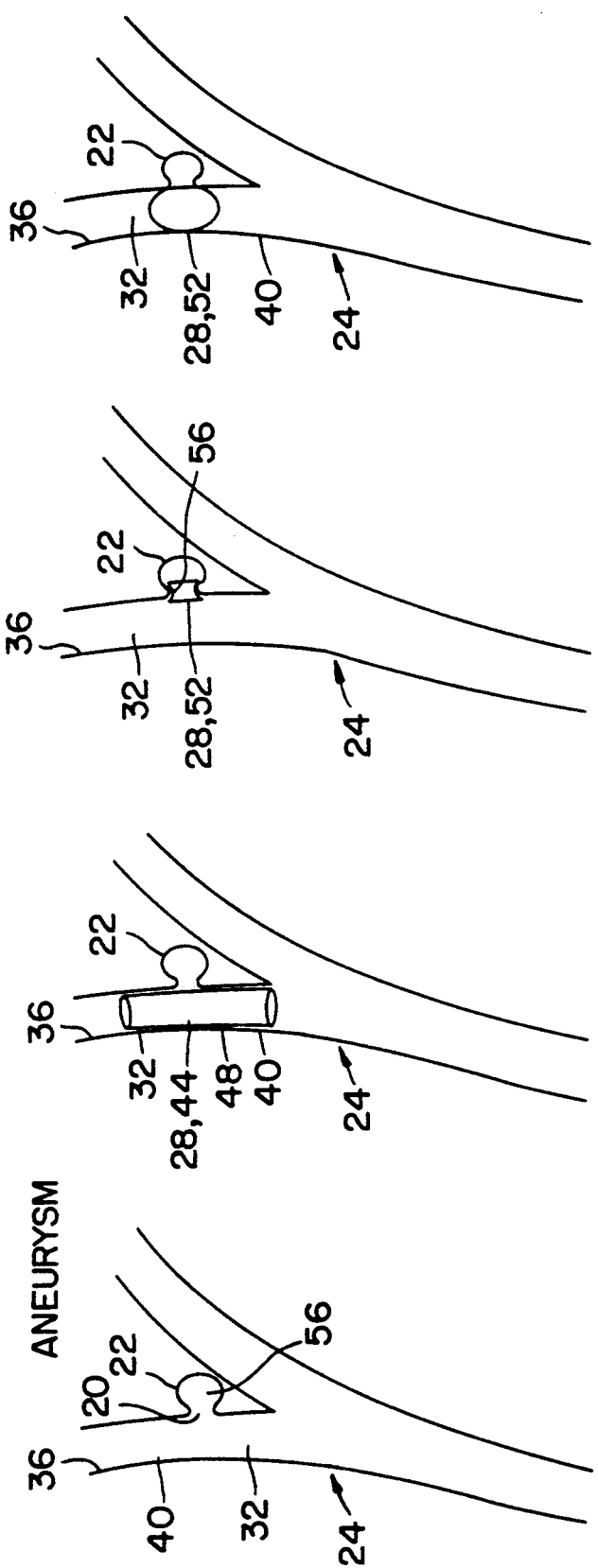

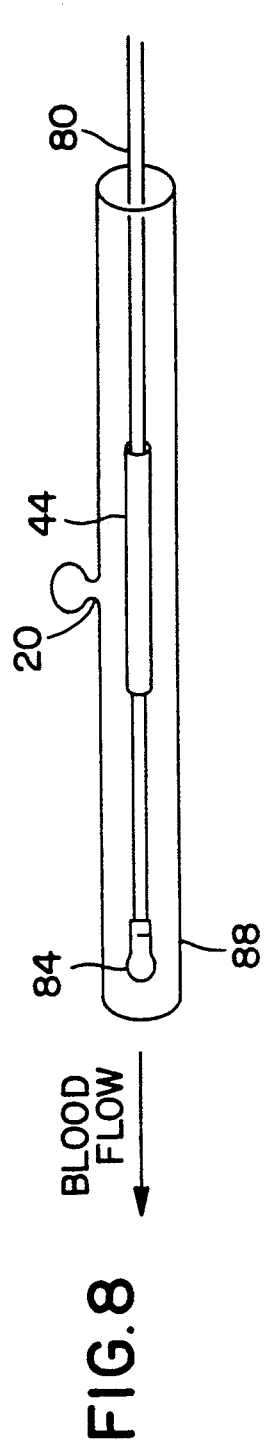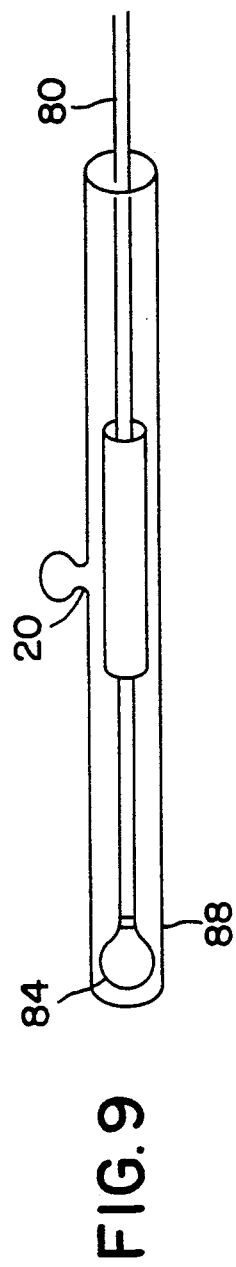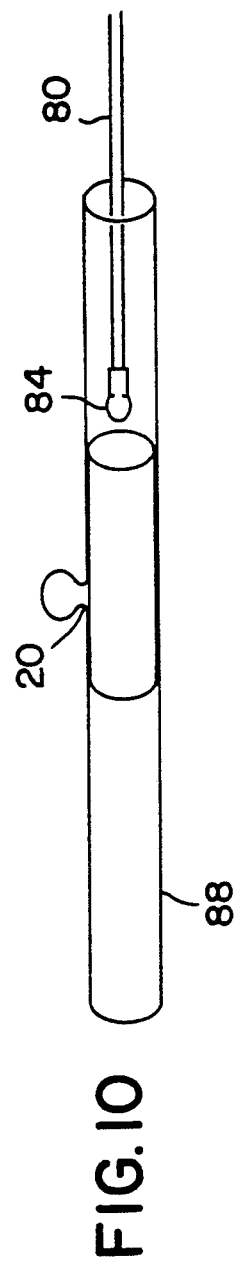

INTRAVASCULAR HYDROGEL IMPLANT

FIELD OF THE INVENTION

This invention relates to a method of using a hydrophilic, nontoxic, hydrogel material in a vascular structure such as a vein, artery or vessel to treat a localized abnormal wall of the structure, and a kit suitable for use in performing the method.

BACKGROUND OF THE INVENTION

The medical field of interventional neuroradiology, includes procedures for the treatment of a localized abnormal wall of a vascular structure, such as arteriovenous fistulae and intracranial aneurysms in a vein, artery or vessel. These procedures are delicate, complex and essential to mitigate potential life-threatening fistulae and aneurysms. More specifically, an arteriovenous fistula is basically an opening between the walls of a closely adjacent vein and artery, resulting in a diversion of blood flow from the higher pressure artery to the lower pressure vein. The flow of blood thus diverted, does not reach portions of the body downstream of the fistula.

An aneurysm is basically a ballooning of a blood vessel at an abnormal wall portion of the vessel which is stretched or distended into a shape referred to as a "sac". An intracranial aneurysm is such a ballooning of a vessel in the brain which could result in loss of brain function or death.

Current methods of treating these localized abnormal wall portions of the vascular structure include packing the abnormal wall of the vascular structure with detachable latex or silicone balloons or electrically detachable platinum coils. In the case of intracerebral aneurysms, the placement of any material (balloon, coil) into the thin-walled aneurysm sac has been known to cause catastrophic rupture of the aneurysm, either by direct perforation, or due to changes in the pressure/flow dynamics during manipulation of the aneurysm. In treating large aneurysms, multiple balloons/coils are needed, with resultant intraaneurysmal blood clot formation. This clot may either: 1) lyse, causing reappearance of the aneurysm with new risk of hemorrhage; or 2) fragment, with clot emboli causing varying degrees of cerebral ischemia, including devastating cerebral infarction.

In the case of carotid-cavernous fistulae, difficulties may arise if the vascular structure is too small to accept a balloon or coil delivery catheter. If the opening is large, the balloon/coil may "herniate" into the artery, resulting in stenosis/occlusion of the internal carotid artery or of one or more of its branches.

Because of these potentially disastrous complications, these procedures are technically difficult, and may be performed only by highly trained individuals.

Metallic stents are not favored for use in vessels and ducts because they rust and are not effective.

Therefore, it is desirable to have a new method, and an apparatus for use with the method, to treat a localized, abnormal wall of a vascular structure.

Among the objects of the invention are to provide a method of using a hydrogel material as an implanted intravascular device for the treatment of certain vascular abnormalities, such as aneurysms, fistulae, or tears of a vessel wall; a method for the delivery, placement and implantation of the device using a fluoroscopically guided catheter via the percutaneous puncture of an access vessel; and a kit containing essential apparatus required to practice the methods, to thereby significantly improve treatment of vascular abnormalities.

SUMMARY OF THE INVENTION

In accordance with the invention, a vein, artery or vessel with a peripheral wall defining a cavity and having a localized abnormal wall is treated by inserting a device of a hydrogel material into the cavity; and then hydrating and expanding the hydrogel material until the device occludes the abnormal wall area.

The hydrogel device may be used to treat vascular structures, namely, veins, arteries, and vessels, with abnormal walls such as: fistulae, aneurysms, dural malformation, vascular malformation, and fibromuscular dysplasia. More particularly, vascular structures include: brachiocephalic artery, carotid artery, vertebrae artery; or their branches: intracranially, coronary artery, femoral artery, popliteal artery, iliac artery, abdominal aorta, the portacaval system, splenic artery, gastric artery, hepatic artery, and superior and inferior mesenteric artery.

In one embodiment, the hydrogel device is in the form of a plug which, for example, occludes the neck of an aneurysm to seal off the sac from the cavity of the parent vessel, artery or vein. The plug may be hollow or solid.

In another embodiment, the hydrogel device is in the form of a tubular stent, which for example, occludes a fistula or a neck of an aneurysm and provides a passage in the cavity. (i.e. maintaining potency of the lumen of the parent artery or vein.)

More specifically, a vascular structure with a peripheral wall defining a cavity and having a localized abnormal wall area is treated by:

a) placing a hydrogel material in the cavity such that an outer surface of the hydrogel material spans the localized abnormal wall; and b) hydrating and expanding the hydrogel material to thereby cause the hydrogel material to abut an inner surface of the peripheral wall and occlude the localized abnormal wall such that the abnormal wall is sealed from the cavity.

The vascular structure, also referred to as a parent vessel, artery or vein, may have a variety of configurations such as a branched, Y-shaped structure, where an aneurysm forms adjacent an intersection of branches, or an arteriovenous structure with a closely adjacent vein and artery and an abnormal wall area comprising an opening (fistula) between the closely adjacent vein and artery.

The hydrogel material may simply be used to cut-off flow of blood through the abnormal wall area, such as by plugging the neck of the aneurysm to isolate or seal off the sac while permitting flow through all branches of the vessel. Alternatively, the hydrogel material may be expanded to essentially fill or plug the entire cross-section of a cavity if flow downstream of the abnormal wall is not critical.

In an alternative method, a vascular structure with a localized abnormal wall is treated using a tubular stent by:

a) placing the stent of a hydrogel material in a cavity formed by an inner surface of the vascular structure such that an outer surface of the stent crosses over the abnormal wall; and b) hydrating the stent to expand the wall of the stent to thereby cause the outer surface of the stent to abut the inner surface of the vascular structure at a sealing edge adjacent the abnormal wall, the sealing edge encircling a peripheral extent of the abnormal wall, such that a suitable passage is provided in the cavity through the stent and across the localized abnormal wall.

The hydrogel material is of a polymer network which is capable of absorbing and retaining a significant quantity of water within its network. This water absorption causes the material to expand or swell to a generally predictable degree depending on the initial size and shape. The high water content, flexibility, lack of or negligible toxicity, and strength of the hydrogel material somewhat resemble that of natural body tissue.

Preferably, a hydrogel material used is of the types produced in a process as described in U.S. Pat. No. 4,663,358 incorporated herein by reference.

The hydrogel stent may conveniently be inserted into the vascular structure using a fluoroscopically guided catheter via the percutaneous puncture of an access vessel, such as the femoral artery or vein, jugular vein, carotid artery and the like. The basic procedure begins with placing the tubular stent on a temporary occlusive balloon catheter. The catheter has an outer diameter which is less than the inner diameter of the stent in both its fully hydrated and dehydrated conditions. The catheter has a balloon on its distal end. The catheter with the stent in place is inserted percutaneously into a vessel in communication with the vascular structure to be treated. The stent is guided along by the catheter to the abnormal wall area and then the balloon is inflated to reduce blood flow so that the stent may be held in place while the stent is being expanded. Once the stent is expanded fully, the balloon is deflated. Then, the catheter is removed and the stent is held in place in the vascular structure, by tension.

The hydrogel stent is conveniently provided as a part of kit used in the percutaneous procedure. The kit includes the stent, the balloon catheter and a guide wire for coaxial placement of the stent in the vascular structure.

BRIEF DESCRIPTION OF THE DRAWINGS

FIG. 1 is a schematic view of a vascular structure with an aneurysm.

FIG. 2 is a schematic view of the vascular structure of FIG. 1, with an implanted device of the invention.

FIG. 3 is a schematic view of the vascular structure of FIG. 1, with an alternative implanted device of the invention.

FIG. 4 is a schematic view of the vascular structure of FIG. 1, with the alternative implanted device of the invention in a different arrangement.

FIG. 8 is a schematic view of a delivery system for placement of the stent of the invention.

FIG. 9 is a schematic view of the delivery system of FIG. 8, after inflation of the balloon.

FIG. 10 a schematic view of the delivery system of FIG. 8, after removal of the catheter.

DETAILED DESCRIPTION OF THE PREFERRED EMBODIMENTS

Figure 5:
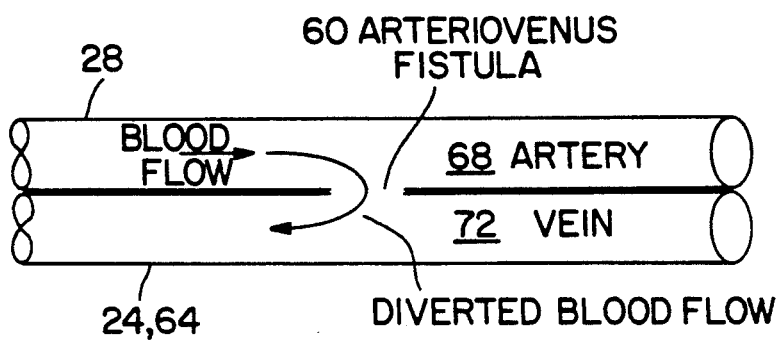
FIG. 5 is a schematic view of a vascular structure with an arteriovenous fistula.

FIG. 1 illustrates an abnormal wall area 20, also referred to as a localized abnormal wall, consisting of an aneurysm 22 at a branch of a vascular structure 24. The term vascular structure refers to a vein, artery or vessel. More particularly, vascular structures include: brachiocephalic artery, carotid artery, vertebrae artery; or their branches: intracranially, coronary artery, femoral artery, popliteal artery, iliac artery, abdominal aorta, the portacaval system, splenic artery, gastric artery, hepatic artery, and superior and inferior mesenteric artery.

As shown in FIG. 2, a preferred embodiment of a hydrogel device 28 of the invention, is placed in the vascular structure 24, to treat the aneurysm 22. As shown in FIGS. 1 and 2, the vascular structure 24 has a cavity 32 defined by an inner surface 36 of a peripheral wall 40 of the vascular structure 24. The hydrogel device 28 is in the form of a tubular stent 44, which becomes expanded by uptake of water from blood present in the vascular structure 24, and held in place essentially permanently by tension between an external surface 48 of the stent 44 and the inner surface 36 of the vascular structure 24.

In one embodiment, the hydrogel stent 44 may conveniently be inserted into the vascular structure 24 using a fluoroscopically guided catheter via the percutaneous puncture of an access vessel, such as the femoral artery or vein, jugular vein, carotid artery and the like. The basic procedure begins with placing the tubular stent 44 on a balloon catheter. The catheter with the stent 44 in place is inserted percutaneously into a vessel in communication with the vascular structure 24 to be treated. The stent 44 is guided along by the catheter to the abnormal wall area 20 and then the stent 44 is held in place while it is expanded. After expansion, the catheter is removed and the stent 44 is held in place in the vascular structure 24, by tension. This procedure is more fully described below.

As shown in FIGS. 3 and 4, the hydrogel device 28 comprises an alternative embodiment in the form of a plug 52 which, upon expansion by water uptake from blood, occludes or seals off the neck 56 of the aneurysm 22 (FIG. 3); or is expanded by uptake of water to occlude both the neck 56 of the aneurysm 22 and the entire cross-section of the cavity 32 of vascular structure 24 in the vicinity of the aneurysm 22 (FIG. 4).

The device 28 of the invention may also be used in the stent 44 or plug 52 form to treat vascular structures with abnormal walls such as fistulae or tears of a vessel wall. An example of an arteriovenous fistula 60 in an arteriovenous vascular structure 64 is shown in FIG. 5, where the blood flow from an artery 68 is diverted to a vein 72 due to the relatively lower pressure of the vein 72.

Figure 6:
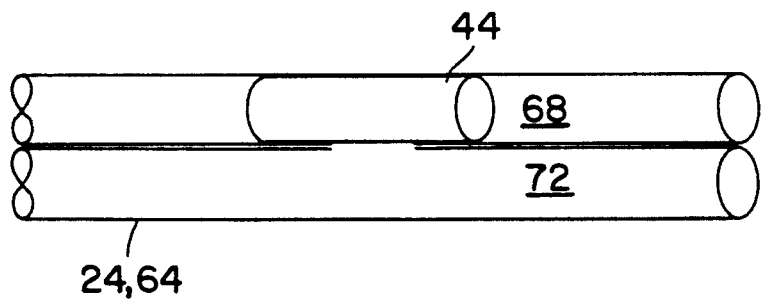
FIG. 6 is a schematic view of the vascular structure of FIG. 5, with an implanted device of the invention.

Accordingly, in another preferred embodiment, as shown in FIG. 6, the stent 44 is placed so as to overlie the opening or fistula 60 between the vein 72 and the artery 68 so as to occlude the fistula 60, permit flow through the stent 44 and thus restore flow toward a direction downstream of the stent in the artery 68.

It should be appreciated that the stent 44 is preferably inserted into the artery 68, however, insertion of the stent 44 into the vein 72 is also possible.

Figure 7:
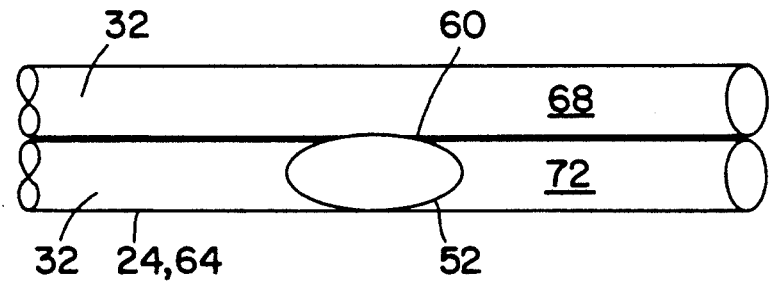
FIG. 7 is a schematic view of the vascular structure of FIG. 6, with an alternative implanted device of the invention.

In still another alternative embodiment, the hydrogel plug 52 may be used to occlude the fistulae 60 and further to occlude the cross-section of the cavity 32 of either the vein 72 or artery 68 if desired, depending on the application (FIG. 7).

An important factor in the success of the method is the choice of the hydrogel material. Recently, new hydrogel materials particularly those derived from poly(vinyl alcohol) have become available, as described in U.S. Pat. No. 4,663,358 incorporated herein by reference. These polymeric hydrogels have a high capacity to absorb and retain water, while the cross-link network prevents dissolution of the individual chains. The high water content, rubbery consistency, low toxicity and low interfacial tension make hydrogels resemble, to some degree, natural tissues. Hydrogels from poly(vinyl alcohol) (PVA) units, provide desired mechanical strength without the need for a cross-linking agent, which may have an adverse effect when implanted. It is surmised that the integrity of the hydrogel material is primarily derived from hydrogen bonding and the large number of small crystallites. Because of the high tensile strength of the PVA hydrogels, they may be manufactured into very thin but strong devices.

Thus, the stent consists essentially of a hydrogel initially in a less than fully hydrated condition. The hydrogel is formed of a PVA polymer with a degree of polymerization sufficient to form a three dimensional network of polymer crystallites with interspaces between the polymer crystallites. When fully hydrated, the hydrogel stent comprises water in an amount up to about 99% by weight of the hydrogel, with at least a portion of the water occupying the interspaces. The hydrogel stent has a tensile strength and elasticity at least equal to the tensile strength and elasticity of the vascular structure. Preferably, the tensile strength is at least about 10 Kg/cm$^2$ and the water content is in the range of 50 to 98% by weight.

While metallic stents are currently being used in vessels and ducts in the body for various reasons, it has been found that the hydrogel stent possesses important properties which render it useful to treat vascular abnormalities by way of internal implant. Key features of the stent as observed during implant include:

a) Variable Size—able to be placed in vessels as small as 4-5 mm internal diameter.

b) Thin Walled—lined the parent artery without significant decrease in overall lumen cross-sectional area.

c) Smooth—the walls of the stent were non-thrombogenic, and there was no significant intimal hyperplasia due to its presence.

d) Hydrophilic—the material absorbed water over a defined period of time (less than 60 min) and expanded the device. The stent was easily introduced into small vessels, followed by stent expansion to a snug fit within the vessel.

e) Flexible and Pliable—provides a smooth transition between the stented segment over the localized abnormal wall and adjacent wall; and is flexible even when mounted on the delivery catheter to permit access through tortuous vessels to the localized abnormal wall area.

The shape of the hydrogel stent 44 is that of a hollow tube, which may be cut to nearly any desired length. The wall thickness is also variable, between 25-100 microns, as is the inner diameter of the tube. These variations in tube length and diameter are controlled during manufacturing, and are important because of the variability in sizes of vascular structures and the localized abnormal wall to be treated. The thickness of the wall of the device after absorption is a key factor in the success or failure of these devices. In general, the thinnest wall possible is most desired. Obviously, as wall thickness increases, there is less lumen caliber (passage cross-section of area). Also, abrupt changes in diameter, such as at the inlet and outlet of the stent, will produce alterations in the laminar blood flow, with possible resultant thrombus (clot) formation, separation of the device from the wall of the vascular structure, or even theoretically, aneurysm formation at that site.

The final outer dimension attained by the device after water absorption depends on: 1) initial diameter of the dehydrated stent; and 2) thickness of the wall of the device (i.e. the thicker the wall, the more water which is absorbed, and hence, the larger the final dimensions). Generally, the initial tube outer diameters are between 1 and 3 mm. The degree of expansion upon water uptake ranges from 1:2 and 1:4. The rate of expansion is greatest in distilled water, less in saline and lowest in human or animal blood.

It has been determined that the hydrogel material described above will expand essentially completely in less than 60 minutes, usually 20 to 40 minutes. It will remain expanded despite expected variations in blood chemistry and only becomes dehydrated and contracted upon contact with alcohol in amounts so great that death by alcohol toxicity would be caused before the stent would become dislodged. The hydrogel material described above, begins to melt at a temperature of about 60 degrees Centigrade, thus death by hyperthermia would be caused at or above about 42 degrees Centigrade, before the stent would dissolve.

EXAMPLE 1

The stent 44 of the invention, was successfully used to treat an aneurysm in the aorta of a rat. An aneurysm was created in the rat's aorta. The aorta had an internal diameter of about 3 mm (millimeters).

A tubular stent 1 cm (centimeter) long, 1.8 mm in external diameter and with a wall thickness of 75 microns in a dehydrated state, was inserted into the aorta and held in place over the neck of the aneurysm for about 20 minutes, until it expanded to an exterior (outer) diameter of 3 mm.

The condition of the aorta 30 days after implantation of the tubular stent demonstrated that the procedure was successful as indicated by:

a) patency of the aorta with the stent in place;

b) lack of filling of the aneurysm;

c) no significant reduction in vessel lumen (cross-sectional area of the parent artery);

d) no detachment or migration of the stent; and e) the pathology of post-mortem showed no fibroblast foreign body reaction or neo-intima.

EXAMPLE 2

The stent 44 of the invention was successfully used to treat an aorta vena cava fistula in a rat. Prior to creation of the fistula, the aorta had an internal diameter of about 2.8 mm and the vena cava had an internal diameter of about 3.8mm. The fistula was created between the vein and aorta as shown in FIG. 10, causing blood from the higher pressure aorta vessel to be diverted into the vena cava. The enlarged vena cava is clearly evident. A tubular stent 1 cm long, 1.8 mm in external diameter and with a wall thickness of 75 microns in a dehydrated state was inserted into the aorta and held in place for about 20 minutes, until it expanded to an exterior (outer) diameter of 2.8 mm.

The condition of the arteriovenous structure 30 days after implantation of the tubular stent indicated success as per the five factors described in Example 1.

A cross-section of the histology of the stent of the fistula case, (Example 2), was taken about one month after implantation. A cut was made into the vascular structure to remove the portion of the structure with the implanted stent. In FIG. 12, the peripheral wall of the vascular structure is clearly visible as is the outer surface of the hydrogel stent. The stent defines a clearly visible passage or lumen with the post-mortem clot in the cavity of the vascular structure. Pathologic analysis clearly shows:

a) no inflammatory reaction around the stent;
b) no neo-intima lining the inner surface of the stent;
c) no intima build up at the ends of the stent;
d) permanent stationary position of the stent to the vessel wall; and
e) absence of discernable pre-mortem clot/plaque on the inner surfaces of the stents.

The method of the invention, as described in Examples 1 and 2, was conducted on a total of ten rats. All of the rats survived the procedure, however, complications arose in three of the ten trials. One rat developed thrombosis of the distal abdominal aorta, but had excellent collateral circulation. The thrombosis was caused by tight closure of aortotomy, due to the insertion method used. Two rats died due to repeated attempts to inject dye.

In all ten cases, success was indicated by lack of gangrene in the tail and lack of heart failure. That is, in the case of the fistula, absence of gangrene in the tail and absence of heart failure indicated that the stent remained in place, closing the fistula. Thus, although death occurred in some cases, post-mortem evidence showed the intended result was achieved.

Although not limited to any particular method for inserting the hydrogel device of the invention, preferably, the device is delivered and placed using a fluoroscopically guided catheter via the percutaneous puncture of an access vessel (femoral artery, femoral vein, internal jugular vein, carotid artery, etc).

As shown in FIGS. 8, 9 and 10, a basic procedure includes placing the tubular stent 44 on a balloon catheter 80 (FIG. 8). The catheter 80 has an outer diameter which is less than the inner diameter of the stent in both its fully hydrated and dehydrated conditions, and has a balloon 84 on the distal end of the stent 44. The catheter 80 with the stent 44 in place is inserted percutaneously into a vessel 88 in communication with the vascular structure 24 to be treated. The stent 44 is guided along by the catheter 80 to the abnormal wall area 20 and then the balloon 84 is inflated to reduce blood flow so that the stent may be held in place while it is expanded (FIG. 9). Once the stent 44 has been expanded, the catheter 80 is removed and the stent 44 is held in place in the vascular structure 24, by tension (FIG. 10).

The hydrogel stent is conveniently provided as a part of kit used in the percutaneous procedure. The kit includes the stent 44, the balloon catheter 80 and a guide wire 90 for coaxial placement of the stent in the vascular structure.

Advantageously, the method and apparatus of the invention will significantly improve the treatment of certain vascular lesions in humans, including arteriovenous fistulae, traumatic vascular lesions, some aneurysms, other abnormal wall areas or localized abnormal wall, as well as having other applications.

We claim:

1. A method of treating a vascular structure, the vascular structure being at least one selected from the group consisting of artery, vein and vessel, the vascular structure having an inner surface and a peripheral wall defining a cavity and having a localized abnormal wall, comprising:

a) placing a tubular stent in the cavity, the stent having a outer surface and an inner surface, such that the outer surface of the stent spans the localized abnormal wall, the stent consisting essentially of a hydrogel in a less than fully hydrated condition, said hydrogel being formed of a polymer with a degree of polymerization sufficient to form a three dimensional network of polymer crystallites with interspaces between the polymer crystallites, and when fully hydrated, water in an amount up to about 99% by weight of the hydrogel, with at least a portion of the water occupying the interspaced; and b) hydrating and expanding the tubular, hydrogel stent to thereby cause the outer surface of the stent to abut the inner surface of the vascular structure at a sealing edge encircling a peripheral extent of the localized abnormal wall, such that a suitable passage is provided through the stent and across the localized abnormal wall.

2. The method according to claim 1, wherein the localized abnormal wall comprises an arteriovenous fistula, and the sealing edge of the stent encircles the peripheral extent of the fistula to seal the fistula from the cavity.

3. The method according to claim 1, wherein the localized abnormal wall comprises an aneurysm with a neck opening into the cavity of the vascular structure and the stent having the outer surface occluding the peripheral extent to the neck opening.

4. A method of treating a vascular structure, the vascular structure being at least one selected from the group consisting of artery, vein and vessel, the vascular structure having a localized abnormal wall, the localized abnormal wall comprising an aneurysm with a neck opening into the cavity of the vascular structure, a) placing a hydrogel plug in the neck opening to occlude the opening, said plug consisting essentially of a hydrogel in a less than fully hydrated condition, the hydrogel formed of a polymer with a degree of polymerization sufficient to form a three dimensional network of polymer crystallites with interspaces between the polymer crystallites, and when fully hydrated, water in an amount up to about 99% by weight of the hydrogel, with at least a portion of the water occupying the interspaces; and b) hydrating and expanding the hydrogel plug to thereby cause the hydrogel plug to occlude the neck opening such that the localized abnormal wall is sealed from the cavity of the vascular structure.

5. A method of treating a vascular structure, the vascular structure being at least one selected from the group consisting of artery, vein and vessel, the vascular structure having a localized abnormal wall, the localized abnormal wall comprising an arteriovenous fistula, a) placing a hydrogel plug in the fistula, said plug consisting essentially of a hydrogel in a less than fully hydrated condition, the hydrogel formed of a polymer with a degree of polymerization sufficient to form a three dimensional network of polymer crystallites with interspaces between the polymer crystallites, and when fully hydrated, water in an amount up to about 99% by weight of the hydrogel, with at least a portion of the water occupying the interspaces; and b) hydrating and expanding the hydrogel plug to thereby cause the hydrogel plug to occlude the fistula.

6. The method according to any one of claims 1, 2, 3, 4 and 5 wherein the hydrogel is a porous poly(vinyl alcohol) hydrogel which has a tensile strength greater than about 10 kg/cm$^2$, water content of 50 to 98% by weight and is prepared by dissolving poly(vinyl alcohol) in a mixed solvent consisting of water and an organic solvent, followed by crystallization of poly(vinyl alcohol) at temperatures lower than room temperature.

* * * * *